(12) United States Patent
Furman

(10) Patent No.: US 7,843,558 B2
(45) Date of Patent: Nov. 30, 2010

(54) OPTICAL INSPECTION TOOLS FEATURING LIGHT SHAPING DIFFUSERS

(75) Inventor: Dov Furman, Rehovot (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 240 days.

(21) Appl. No.: 12/145,712

(22) Filed: Jun. 25, 2008

(65) Prior Publication Data

US 2009/0323053 A1    Dec. 31, 2009

(51) Int. Cl.
*G01N 21/00* (2006.01)
(52) U.S. Cl. .................. 356/237.1; 356/237.2
(58) Field of Classification Search .... 356/237.1–237.5
See application file for complete search history.

(56) References Cited

U.S. PATENT DOCUMENTS

| | | | |
|---|---|---|---|
| 4,521,075 A | 6/1985 | Obenschain et al. | |
| 4,619,508 A | 10/1986 | Shibuya et al. | |
| 5,040,872 A | 8/1991 | Steinle | |
| 5,699,447 A | 12/1997 | Alumot et al. | |
| 6,169,634 B1 | 1/2001 | Sirat | |
| 6,367,935 B1 | 4/2002 | Wang et al. | |
| 6,577,429 B1 | 6/2003 | Kurtz et al. | |
| 6,724,473 B2 | 4/2004 | Leong et al. | |
| 6,798,505 B2 | 9/2004 | Karpol et al. | |
| 6,830,189 B2 | 12/2004 | Tsikos et al. | |
| 6,927,847 B2 * | 8/2005 | Yoshida et al. | 356/237.4 |
| 6,947,220 B1 | 9/2005 | Soskind | |
| 7,110,105 B2 * | 9/2006 | Yoshida et al. | 356/237.4 |
| 7,180,586 B2 * | 2/2007 | Neumann et al. | 356/237.5 |
| 7,295,305 B2 * | 11/2007 | Yoshida et al. | 356/237.5 |
| 7,586,959 B2 | 9/2009 | Korngut | |
| 7,630,069 B2 * | 12/2009 | Naftali et al. | 356/237.2 |
| 7,659,973 B2 * | 2/2010 | Furman et al. | 356/237.2 |
| 2003/0123159 A1 | 7/2003 | Morita et al. | |
| 2004/0146295 A1 | 7/2004 | Furman et al. | |
| 2005/0264797 A1 | 12/2005 | Nakano et al. | |
| 2006/0163503 A1 | 7/2006 | Urano et al. | |

(Continued)

FOREIGN PATENT DOCUMENTS

EP    1521110 A    4/2005

(Continued)

OTHER PUBLICATIONS

MEMS Optical Online Article "Diffractive Defusers", retrieved from http://www.memsoptical.com/techinfo/datasheets/DD-en-060516.pdf, on Apr. 22, 2008; 2pp.

(Continued)

*Primary Examiner*—Michael P Stafira
(74) *Attorney, Agent, or Firm*—SNR Denton US LLP

(57) ABSTRACT

An optical inspection system or tool can be configured to adjust the distribution of light by using one or more diffusers. The diffusers can be variable in some embodiments. For example, the angular or spatial distribution of the illumination can be adjusted to minimize intensity of illumination outside of an imaged area to thereby reduce illumination loss. The angular or spatial distribution may additionally or alternatively be adjusted so that the illumination across an illuminated area is substantially uniform. The use of one or more diffusers may aid in the inspection of semiconductor objects including, but not limited to, semiconductor wafers and the like.

14 Claims, 8 Drawing Sheets

U.S. PATENT DOCUMENTS

| | | | |
|---|---|---|---|
| 2006/0244957 A1* | 11/2006 | Furman et al. | 356/237.4 |
| 2006/0244958 A1* | 11/2006 | Furman et al. | 356/237.4 |
| 2007/0013903 A1* | 1/2007 | Furman et al. | 356/237.5 |
| 2007/0070302 A1 | 3/2007 | Govorkov et al. | |
| 2008/0037933 A1 | 2/2008 | Furman et al. | |
| 2009/0323052 A1* | 12/2009 | Silberstein et al. | 356/237.5 |

FOREIGN PATENT DOCUMENTS

| | | | |
|---|---|---|---|
| EP | 1521111 A1 | 4/2005 | |
| JP | 02098919 A | 4/1990 | |
| JP | 07335523 A | 12/1995 | |
| JP | 2003031872 A | 1/2003 | |
| JP | 2003167213 A | 6/2003 | |
| JP | 2006323104 A | 11/2006 | |
| WO | WO 03029875 A2 | 4/2003 | |

OTHER PUBLICATIONS

Office Action dated May 12, 2008, from U.S. Appl. No. 11/236,355, filed Sep. 26, 2005, 11 pages.

Response to Office Action filed Aug. 8, 2008, from U.S. Appl. No. 11/236,355, filed Sep. 26, 2005 12 pages.

Office Action dated Nov. 26, 2008, from U.S. Appl. No. 11/236,355, filed Sep. 26, 2005, 12 pages.

Response to Office Action filed Jan. 13, 2009, from U.S. Appl. No. 11/236,355, filed Sep. 26, 2005 19 pages.

Chinese Application No. 200510138026.3; Decision on Rejection dated Sep. 25, 2009, 6pp.

Chinese Application No. 200510138026.3; Second Office Action dated Jun. 5, 2009, 7pp.

Chinese Application No. 200510138026.6; Second Office Action dated Sep. 5, 2008, 15pp.

Korngut et al., U.S. Appl. No. 60/613,894, filed Sep. 27, 2004, entitled: "Speckle Reduction with Glass Made Stairs", 8pp.

* cited by examiner

OPTICAL INSPECTION TOOLS FEATURING LIGHT SHAPING DIFFUSERS

BACKGROUND

Optical inspection allows for rapid and effective identification of defects in semiconductor objects, which include (but are not limited to) semiconductor wafers, reticles, mask patterns, and other items that are the result of or are used in fabrication of miniaturized electronic devices.

Various illumination and imaging systems have been proposed for optical inspection tools. For example, some systems use lamps or lasers to illuminate the object under inspection, with a detector or an array of detectors used to image areas of interest on the object.

FIG. 1 illustrates a common scheme of dark field illumination typically used in semiconductor inspection systems comprising two-dimensional detectors. An illumination source 104 illuminates a semiconductor object 12 at an oblique angle, often using Kohler illumination. The impingement angle Φ is generally very acute relative to the object plane.

The source emits light 108 with a predefined angular distribution at the focal plane of a lens 106 or other optical elements in the illumination path. The light passes through the lens 106 (and/or other components) and impinges the semiconductor object 12, which is located at the other focal plane of the lens.

As shown in FIG. 2, since the illumination source angular distribution is usually circular and due to the oblique illumination angle, the illuminated area 110 on the semiconductor object is an ellipse. At a typical illumination angle of 15°, the aspect ratio of the ellipse is about 1:4. However, the imaged area 112 of an inspection tool is usually in the shape of a square or a slightly rectangular square (i.e. a rectangle with aspect ratio not far from one). All the illuminated area outside of the imaged area does not reach the tool's detector(s) and therefore can be considered as an illumination loss.

Another problem recognized by the current inventors regarding oblique Kohler illumination in inspection tools is illustrated at FIGS. 3 and 4. FIG. 3 shows a ray trace for two points (A and B) of a non-oblique illumination source 104, i.e., a configuration where object 12 is perpendicular to incoming illumination. In FIGS. 3 and 4, the dashed lines represent ray traces from point A, while the dotted lines represent ray traces from point B. Each point illuminates the same area, A'B', on the object, at different impingement angle ($\Phi_{A1}$ for light from point A, $\Phi_{B1}$ for light from point B).

However, when the illumination is oblique relative to the object, as shown at FIG. 4, the area of each illumination point is different. The illumination from point B at the source impinges the object at a more acute angle ($\Phi_{B2}$) than the angle ($\Phi_{A2}$) for illumination from point A. A closer view of the impingement angles is shown in the magnified view of FIG. 4A. Therefore area B' illuminated by light from point B is larger than area A', representing the area illuminated by light from point A.

A diagram of the illuminated area 110 is shown in FIG. 5; as before, in this example, a circular angular distribution of illumination for an object at an oblique angle results in an ellipse-shaped illuminated area. In this figure, the areas with less dense cross-hatching receive illumination at higher intensity, with the highest intensity in the center. Light from all parts of the source illuminates the center of the illuminated area on the object. However, the periphery of the illuminated area does not receive light from all parts of the source since light from different parts of the source impinges at different angles (with different resulting areas). Therefore, the illuminated intensity is lower moving outward from the center, especially along the major axis of the ellipse.

FIG. 5 also shows two exemplary imaged areas 114A and 114B. If larger area 114A is imaged, the resulting image will likely be degraded due to non-uniform illumination. If the imaged area is set to be smaller than the center of the illuminated area (rectangle 114B), illumination may be more uniform at the cost of higher illumination loss.

SUMMARY

In accordance with one or more aspects of the present subject matter, an optical inspection system or tool can use one or more light shaping diffusers to adjust the angular distribution and/or otherwise change the illuminating light to achieve better results. For example, the shape of an illuminated portion can be adjusted to reduce illumination loss, such as by shaping the illuminated portion to match the shape, and in some embodiments, the size, of the imaged portion. As another example, the angular distribution of the illuminating light can be adjusted so as to reduce or eliminate nonuniformities in the illuminated portion.

In some embodiments, an optical inspection tool can comprise a light source configured to direct light to an object under inspection. The object can include, but is not limited to, a semiconductor wafer, reticle, mask, and the like. The light can impinge on the object to illuminate one or more portions of the object (also referred to as an "illuminated portion"). The tool can comprise an imaging system operative to image at least a portion of the object, with an imaged portion including part of or possibly all of one or more illuminated portions. The tool can comprise one or more light shaping diffusers in an optical path between the light source and the object under inspection. For tools that use multiple illumination paths, a diffuser can be in one or more of the paths. The light from the source may be provided directly to the diffuser, or may pass through one or more other components before reaching the diffuser. The tool can, of course, include other optical components as needed after the diffuser but before the object (e.g. objective and/or focusing lenses), along with suitable components to relay light to the imaging system.

In some embodiments, the illuminated portion may comprise an area on the object that is illuminated at a given time (i.e. all points in the area are illuminated simultaneously). For example, the imaging system may comprise one or more two-dimensional detectors, with the detector(s) configured to image an area that includes some or all of the illuminated area. Some embodiments may use point illumination and/or point detection, wherein an area on the object is illuminated by illuminating various points over time (e.g. by scanning one or more point sources in a pattern on the object). Similarly, point detection may image an area by imaging different points in the area over time. As another example, an object may be illuminated/imaged on a "line by line" basis wherein an area is imaged as a series of one dimensional lines.

It will be understood that "point" and "line" detection are not truly one-dimensional. Instead, as understood by one of skill in the art, a "point" refers to a single pixel, while a "line" is one dimensional in the sense that it is a series of adjacent pixels.

In some embodiments, the shape of the illuminated portion is matched to the shape of the imaged portion. For example, when an area is simultaneously illuminated, the light shaping diffuser can be configured so that the shape of the illuminated area is essentially the same shape as that of the imaging area. By "essentially the same shape," it is meant that the shapes could be identical or similar (in the geometric sense), but exact identity or similarity is not necessarily required. Similarly, the shape of an illuminated point or line can be matched to the imaged point or line.

In certain embodiments, the light shaping diffuser is configured so that angular distribution of light from the light source is converted. For example, the angular distribution may be converted to a rectangular angular distribution from another distribution (including, but not limited to, a circular distribution). As another example, the angular distribution may be converted to a quadrangular angular distribution.

Some implementations of an optical inspection tool can comprise a light shaping diffuser configured to adjust the distribution of light from the light source in order to minimize the intensity of light in the illuminated portion(s) of the object that is not included in the imaged portion. For example, if all points in an area are imaged simultaneously, the angular distribution can be adjusted so that the intensity of the light outside the imaged area is minimized. As another example, if point (or line) illumination/imaging is used, the angular distribution of light can be adjusted to minimize the intensity of the light impinging on the object outside the point (or line) of the object that is imaged.

The diffuser may be configured so that the uniformity of light impinging on the object is improved relative to the uniformity of light were the system to be used without a diffuser. The improvement could result in light that is substantially uniform across all or part of the illuminated or imaged portion. "Substantially uniform" is meant to include not only absolute uniformity, but also a distribution of intensity whose variance, for purposes of an inspection, could be treated as zero.

The diffuser may be especially useful for dark-field illumination modes, but can be used in any mode to adjust the size and/or shape of an illuminated area (or line or point); to match the size and/or shape of the imaged area (or line or point); to minimize the intensity of light outside the imaged area (or line or point); and/or to provide for substantially uniform light across the imaged area (or line or point).

Some embodiments of an optical inspection tool can include a light source and/or other components configured to direct light to an object under inspection so that the object is illuminated in dark-field mode. The tool can further comprise an imaging system operative to image at least a portion of the object. The tool can comprise one or more light shaping diffusers in an optical path between the source and object, with the diffuser(s) configured so that, when impinging on the object, light directed to the object from any given part of the source illuminates essentially the same portion of the object. For example, the diffuser can be configured so that light from various points on the face of the source illuminate essentially the same area on the object.

The light shaping diffuser can comprise a single diffuser or multiple diffusers used in combination. In some embodiments, a diffuser may be a "variable diffuser," i.e. a diffuser that changes the distribution of light differently depending upon which part of the diffuser the light enters. A "variable diffuser" may comprise several discrete diffusers combined into a unit, a diffuser having a stepwise design, and/or may utilize material that provides a continuously-variable effect within a single unit.

An electro-optical inspection method can comprise directing light from a source to an object under inspection to illuminate a portion of the object and imaging some or all of the illuminated portion. The method can comprise diffusing the light prior to when the light impinges on the object. The method can further comprise analyzing at least one image to evaluate its defect status—i.e. to identify or attempt to identify one or more defects or suspected defects. Illuminating the object can include illuminating the object in dark-field mode.

Diffusing the light can include adjusting the angular distribution of the light, including changing the angular distribution to a rectangular or quadrangular angular distribution. Diffusing the light can comprise adjusting the light so that, when it impinges on the object, the shape of the illuminated portion is essentially the same as that of the imaged portion. Diffusing the light can comprise adjusting the light so as to minimize the intensity of light in the part(s) (if any) of the illuminated portion outside of the imaged portion. Diffusing the light can comprise adjusting the light so that light impinging on the object is substantially uniform.

As was noted above, depending upon whether the inspection tool is operating to image all points in an area at a given time or images an area on a point-by-point (or line-by-line) basis, the imaged and/or illuminated portions may be areas, points, or lines.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended Figures, in which like numerals are intended to represent similar or analogous features.

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the instant disclosure includes modifications and variations as come within the scope of the appended claims and their equivalents. The use of headings, numberings, and the like is meant to assist the reader of the specification, and not to limit the subject matter.

Figure 1:
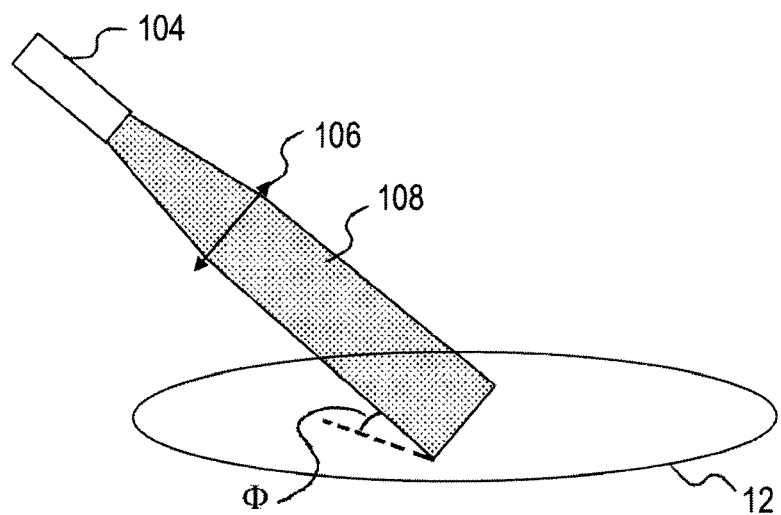
FIG. 1 shows a simplified example of dark field illumination without the use of a diffuser.
Figure 2:
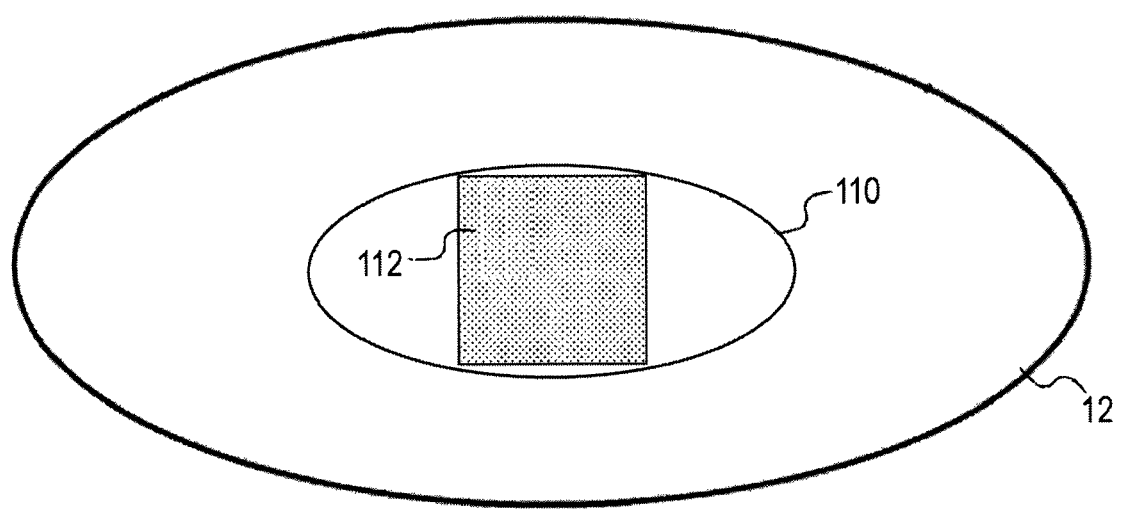
FIG. 2 shows an example of an illuminated and imaged area on a wafer.
Figure 3:
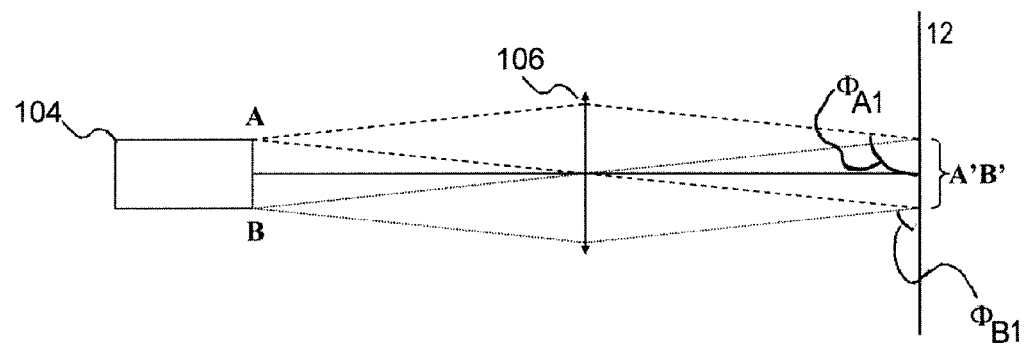
FIGS. 3 and 4 are, respectively, conceptual illustrations of non-uniform illumination when an object is perpendicular and slanted relative to incoming light from an illumination source.
Figure 4:
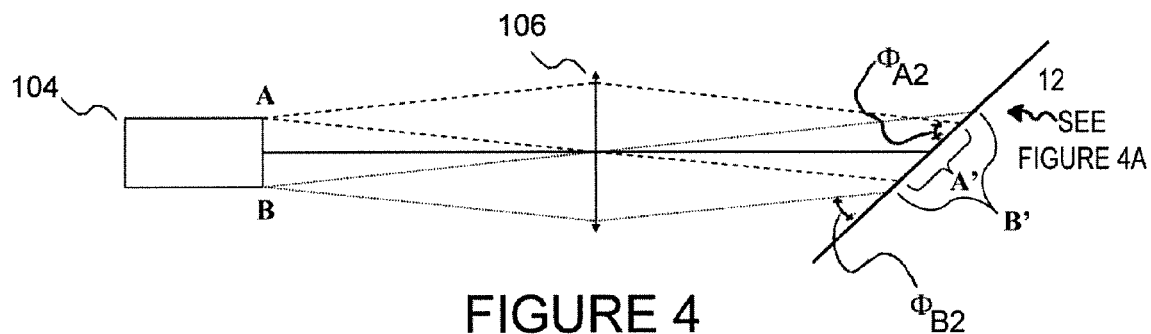
Figure 4A:
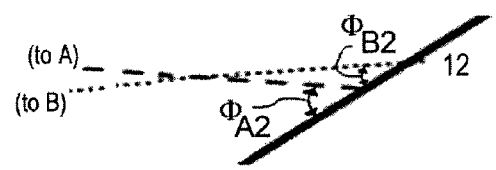
Figure 5:
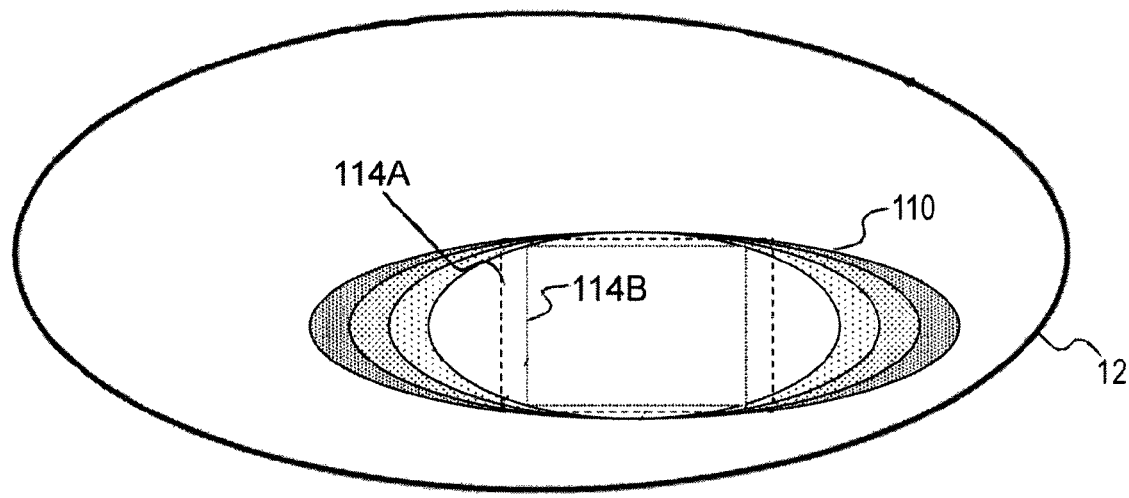
FIG. 5 illustrates an example of non-uniform illumination resulting when an object is slanted relative to an illumination source, along with examples of the relationship between an imaged area and illuminated area of the object.
Figure 6:
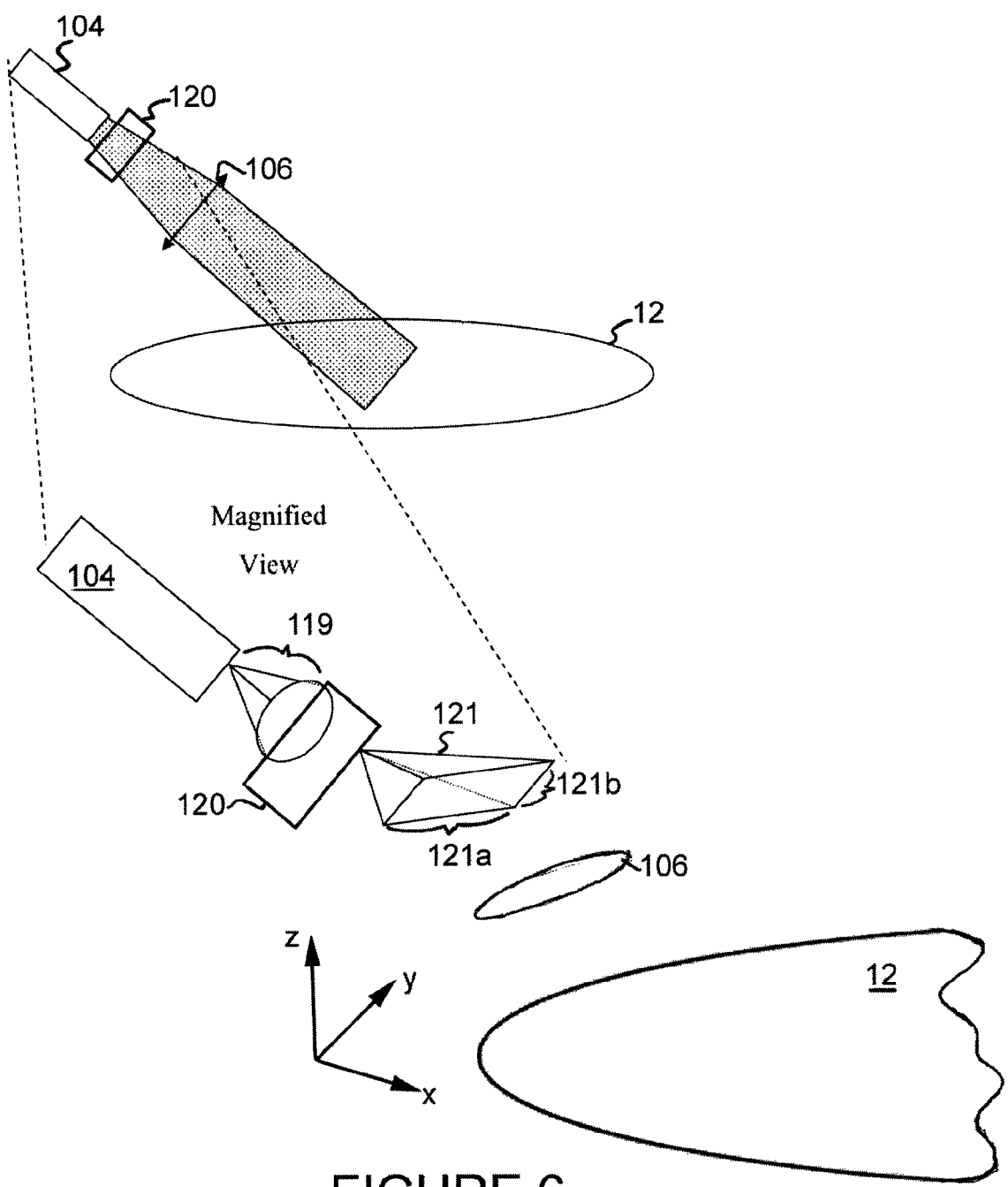
FIG. 6 is a diagram illustrating one example of using a light shaping diffuser in an optical inspection system.

FIG. 6 is a diagram illustrating one example of an illumination system comprising a light shaping diffuser for use in illuminating an object in an optical inspection system. As shown in FIG. 1, an illumination source 104 illuminates a portion of semiconductor object 12 by way of one or more optical components 106 (in this example, a lens). However, in accordance with one or more aspects of the present subject matter, FIG. 6 indicates an example of a light shaping diffuser 120 placed in the optical path between source 104 and object 12. As shown in the inset, light shaping diffuser 120 converts circular angular distribution 119, which is emitted from each point of source 104, to a rectangular angular distribution 121.

The magnified view also shows a portion of object 12 and an x-y-z axis. In this example, the larger axis 121A of the rectangular distribution is parallel to the object plane (the x-y plane in this example), and the smaller axis 121B is at angle to the object plane. Put another way, looking from the illumination source direction where the horizontal axis of the view is parallel to the object plane, the angular distribution looks wide and short. The ratio between the distribution widths of these axes is approximately the sine of the illumination angle (measured relative to the object plane).

Figure 7:
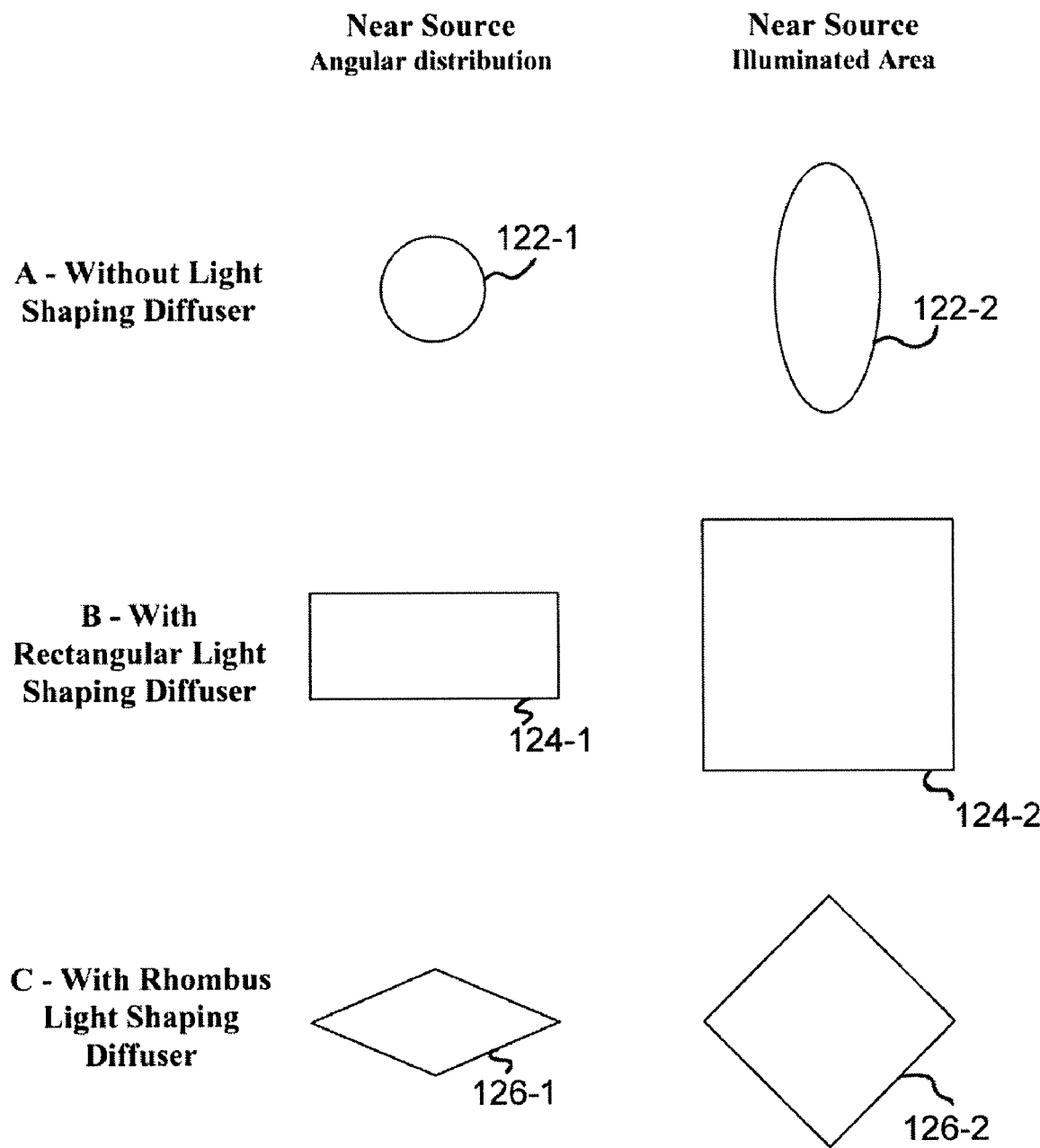
FIG. 7 provides a series of exemplary shapes for illuminated areas.

FIG. 7 provides a series of exemplary shapes for illuminated areas. As shown at A, in an embodiment using an illumination source with a circular distribution, the angular distribution near the source is circular as shown at 122-1, and the shape at the illuminated area near the source is elliptical as shown at 122-2. At B, the effects of a rectangular light-shaping diffuser are shown. After conversion via one or more diffusers to a rectangular distribution, the angular distribution near the source is rectangular as shown at 124-1, while the illumination on the object is square, as shown at 124-2.

The light shaping diffuser can be used to set any requested illumination area, in order to fit the imaged area. For example, if the requested illumination is slightly rectangular, the ratio between the distribution widths may be tuned accordingly.

Another example is when the illumination axis projected on the object plane is not parallel to the axis of the imaged area. This causes the imaged area to be tilted respective to the illumination axis. The light shaping diffuser for this case may be rhombus-like or may have another quadrangular shape in order to fit the tilted images. At C, the effects of a rhombus-shaped diffuser are shown. At 126-1, the angular distribution is a wide rhombus, while at 126-2, the resulting illuminated area is another rhombus, or may even be a tilted rectangle.

Figure 8:
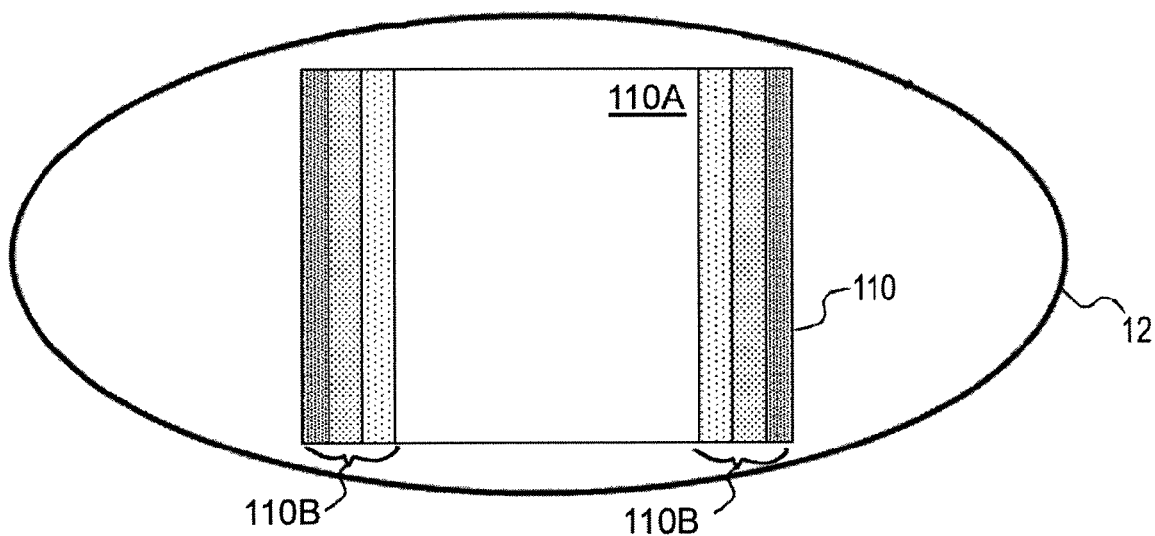
FIG. 8 illustrates an example of non-uniform illumination that can result even when a light-shaping diffuser is used.

FIG. 8 illustrates an example of non-uniform illumination that can result even when a light-shaping diffuser is used. Returning to the rectangular distribution, the problem where each point in the source illuminates a different area on the object may not be solved merely by changing the angular distribution shape or the shape of the illuminated area. As shown in FIG. 8, the illumination density is still not uniform. Instead, the center 110A of the illuminated area 110 has higher intensity relative to that of the periphery 110B.

Figure 9:
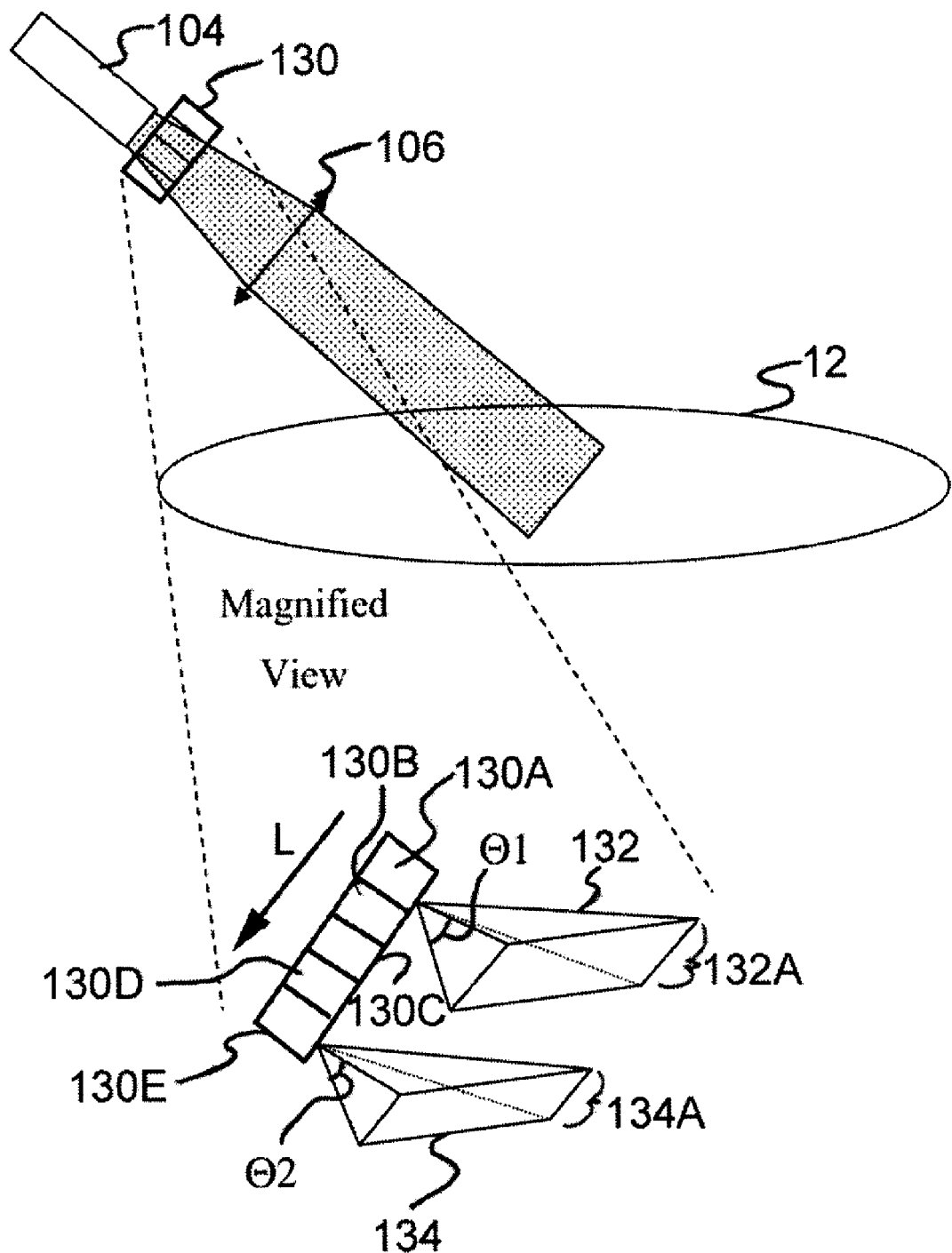
FIG. 9 is a diagram illustrating an example of using a variable light shaping diffuser in an optical inspection system.

FIG. 9 is a diagram illustrating another example of an illumination system comprising a light shaping diffuser for use in illuminating an object in an optical inspection system. An optical inspection system constructed in accordance with one or more aspects of this embodiment can avoid some or all of the non-uniformity of the illumination. As in the examples discussed above, an illumination source 104, optical element 106, and semiconductor object 12 are shown. Instead of a homogeneous light shaping diffuser, though a variable light shaping diffuser 130 is shown in this example. A "variable" light shaping diffuser has different characteristic in at least some of the points along its length (and in some embodiments, has a different characteristic at each point along its length). In this example, the differences result in a smaller angular distribution for points along the length of diffuser toward the object (direction L in FIG. 9). Put another way, the width of the angular distribution in the short axis of the rectangle shape is smaller. As shown in FIG. 9 at the inset, light exiting the diffuser at points farther from the object is distributed at a larger angle ($\Theta_1$) than the angle ($\Theta_2$) of light exiting the diffuser at points closer to the object.

In this example, the angular distribution of each point is tuned so that each light emerging from each point on the source illuminates the same sized area on the inspected object.

The manner in which the variable diffuser changes angular distributions can vary; that is, the angular distribution does not always need to decrease along its length. For example, a variable diffuser can be configured in order to obtain better distribution and/or shape of an illuminated area when the tool is illuminating at an angle to the imaged area axis. The angular distribution may change according to the point at which light enters the diffuser along its width, for example, or the distribution may change according to where light enters the diffuser along both its length and width.

The variable light shaping diffuser may be a single element with continuously variable characteristics or may vary in steps. The steps are shown in FIG. 9 as a series of different areas 130A, 130B, 130C, 130D, and 130E. As another example, the diffuser may comprise multiple light shaping diffusers connected in any way known in the art. For example, areas 130A-E may represent different areas of one unitary diffuser 130 having areas of different characteristics, or areas 130A-E may represent a group of diffusers bonded or arranged together to comprise diffuser 130.

The examples discussed above are not intended to be limiting. For instance, the present subject matter is not limited to single light shaping diffuser or a single arrangement of diffusers at one point in an optical path. Rather, in some embodiments, multiple light shaping diffusers can be used in order to achieve the requested angular distribution. In addition, lenses or other optical elements may be placed before the light shaping diffuser and/or after the light shaping diffuser. If multiple light shaping diffusers are used, optical components may lie between these diffusers.

The present subject matter is not limited to dark field illumination only. For example, light shaping diffusers can be used to tune the illumination area in bright field, orthogonal dark field, or any type of illumination. In bright field illumination, for example, light shaping diffusers may be used for changing the illumination area from a circle to a square or rectangle, depending on what and how imaging is used.

The present subject matter is not limited to Kohler illumination only. Other methods of illumination may be used, such as critical illumination. In critical illumination, the light shaping diffusers will not change the spatial distribution of light at the illuminated portion, but instead will change the angular distribution of the light impinging the object.

In some embodiments, multiple diffusers may be used in combination. For example, two diffusers may be used, with one diffuser shaping the angular distribution of light that impinges the object, while the other shapes the spatial distribution of the light impinging the object.

Figure 10:
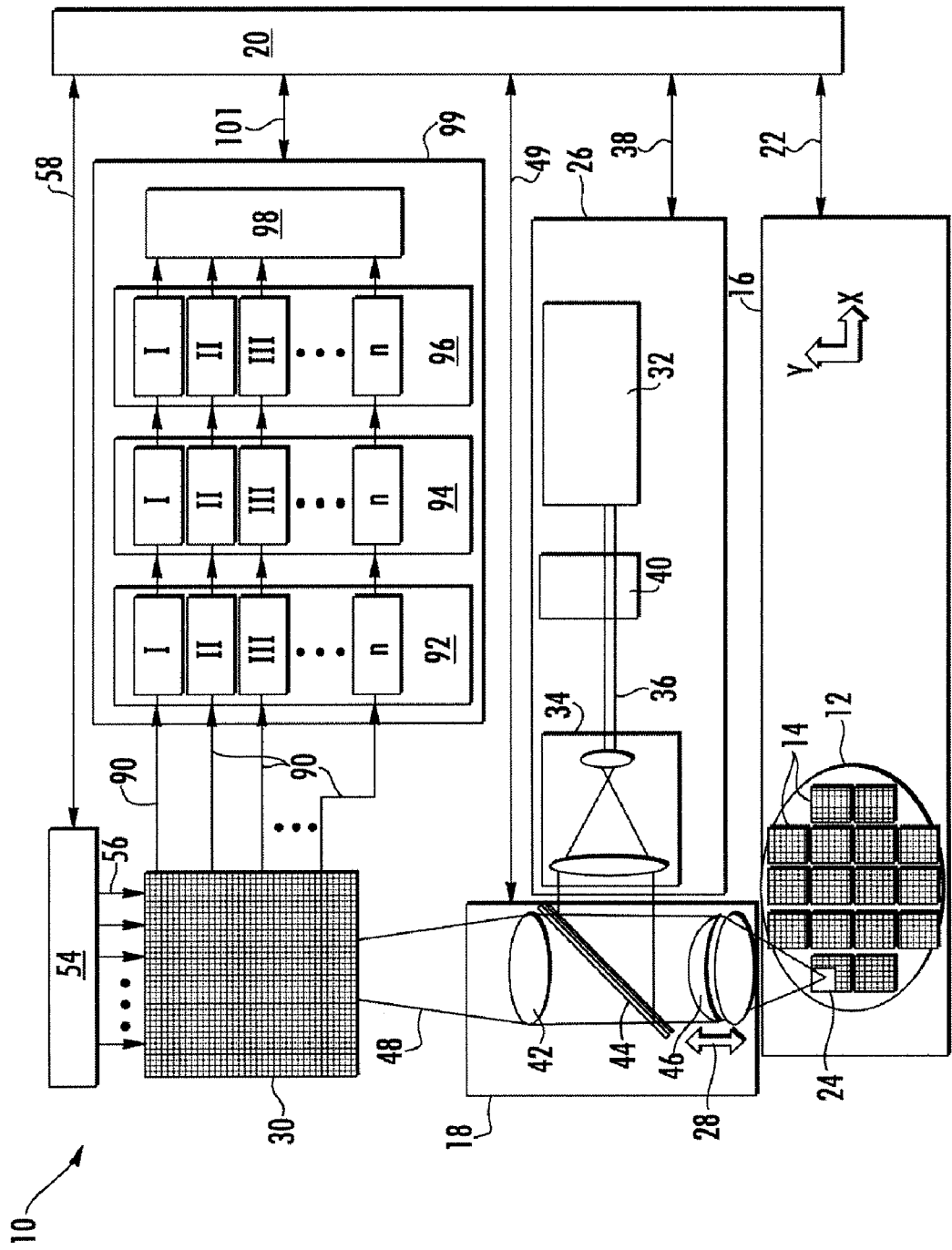
FIG. 10 is a block diagram showing illumination, imaging, and control components in an exemplary optical inspection tool.
Figure 11:
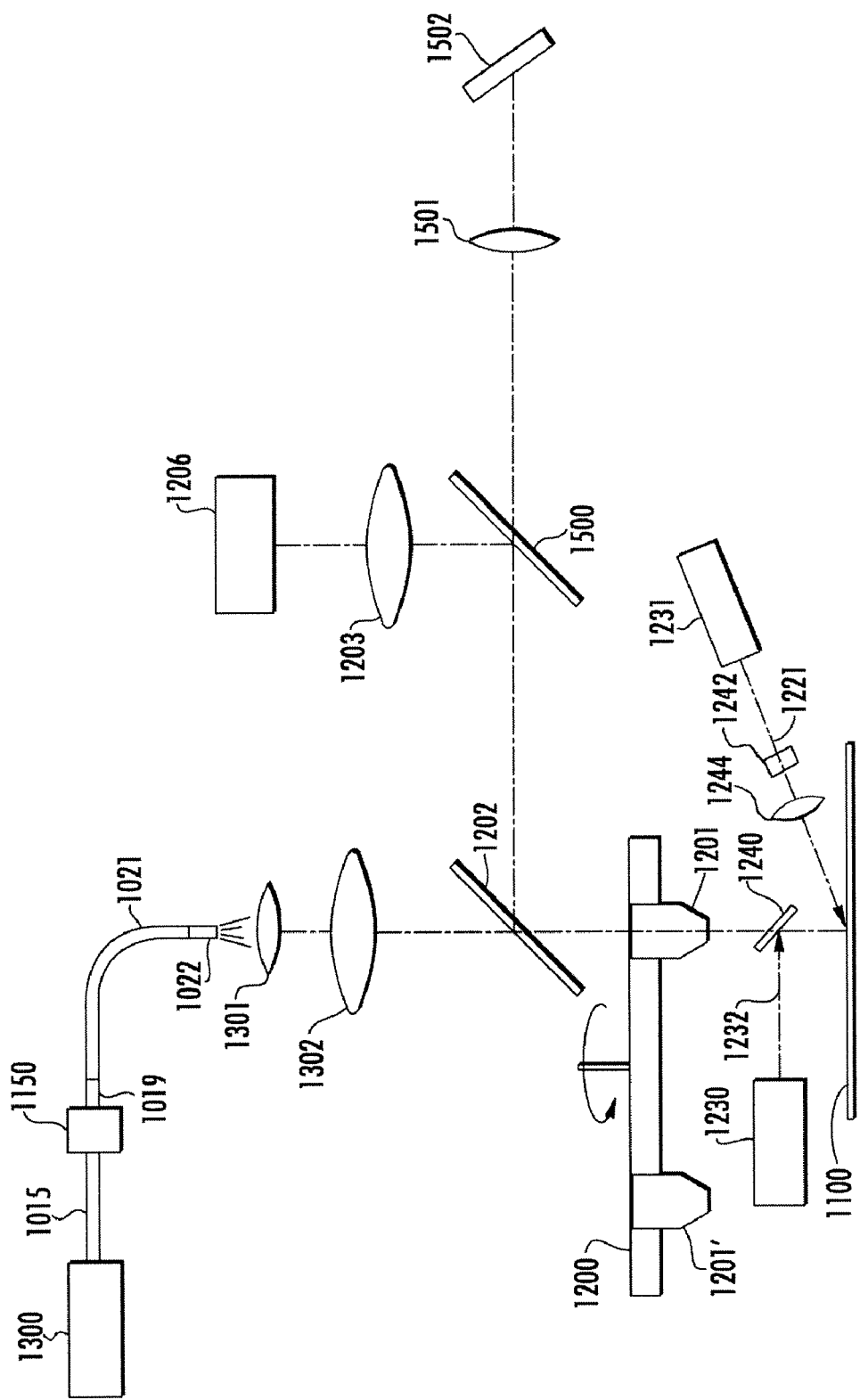
FIG. 11 is a block diagram showing additional aspects of imaging and illumination in an exemplary optical inspection tool.

FIG. 10 is a block diagram showing illumination, imaging, and control components in an exemplary optical inspection tool and FIG. 11 is a block diagram showing additional aspects of imaging and illumination in an exemplary optical inspection tool.

In this example, FIG. 10 is a schematic diagram illustrating an exemplary embodiment of a system for fast on-line electro-optical detection of wafer defects, while FIG. 11 shows a schematic illustration of an object inspection system utilizing a laser source and a fiber optical delivery bundle in an exemplary inspection tool. For instance, the tool may comprise a Negevtech 3320, 3370, or other model optical inspection tool (available from Negevtech, Ltd. of Rehovot, Israel), modified to include a light-shaping diffuser or diffusers for one or more illumination modes.

Additional details regarding exemplary aspects of an optical inspection system can be found in U.S. patent application Ser. No. 10/345,097, published as U.S. Patent Application No. 2004-0146295 A1, which is incorporated by reference herein for all purposes in its entirety to the extent it is not in conflict with the present subject matter. However, it is to be noted that the illumination principles discussed herein can be used in any suitable inspection system that creates an image of an object at a focal plane.

As shown in FIG. 10, inspection tool 10 can include a focal plane assembly 30 comprising pixels from multiple two-dimensional detectors. Focal plane assembly 30 is configured so that light from an article being inspected is sensed by detectors arranged in accordance with one or more aspects discussed below. In this example, assembly 30 is depicted as providing a continuous surface. It will be recognized that, in different embodiments and depending on the optical configuration and state of the tool, a discontinuous surface may be presented in some instances.

In operation, the dies 14 of wafer 12 can be illuminated in any suitable manner, such as by laser light from pulsed illumination system 26. Light 48 represents rays of light scattered, reflected, and diffracted by the wafer. This light can be collected using imaging optics 18. In this example, imaging optics 18 comprise a beam splitter 44 (used in illuminating wafer 12 with light from laser system 26), focusing lens 42, and an objective lens 46 which may be adjusted using an auto-focus system 28 (not shown in detail). In this example, focusing lens 42 focuses light 48 onto focal plane assembly 30 and defines the focal plane of imaging optics 18. However, the actual content and arrangement of a particular set of imaging optics can vary. Particularly, the imaging optics 18 shown in this example are simplified for purposes of explaining general principles of an inspection tool.

In this example, a patterned semiconductor wafer 12 featuring a plurality of wafer dies 14 is placed and aligned on a continuous moving XY translation stage 16 to impart relative motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging optics 18 in a serpentine (or other) pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution. Control system 20 can comprise any suitable type or arrangement of components used to orchestrate the inspection process, including, for example, a microprocessor-based controller, a general-purpose or specialized computer system, and the like.

In this example, illumination system 26 includes a repetitively pulsed laser 32, a laser beam expander 34, a laser beam light path 36, control/data links 38, and a crystal 40 having non linear optical properties and serving as a 'second harmonic' or 'third harmonic' generating crystal. This type of illumination system enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. As will be noted below, in some embodiments, the illumination system can comprise additional components used to adjust the illumination. Furthermore, in embodiments in which the intensity or other aspects of the illumination can be tuned, appropriate control/data links can be used to command desired illumination levels and/or other characteristics from the pulsed laser 32 and other components.

Briefly, FIG. 11 illustrates exemplary components associated with illuminating an object in an inspection system. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 11 shows a bright field illuminating laser source 1300 delivering its output beam 1015 into an optical delivery fiber bundle 1021, preferably by means of a laser to fiber coupler 1150. This optical fiber bundle 1021 provides both uniform illumination on the sample and coherence breaking of the laser illumination. In some embodiments, only a single fiber bundle is used, but it is to be understood that a serially-arranged fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006 published as US20080037933A1 on Feb. 14, 2008, which is incorporated by reference herein for all purposes in its entirety to the extent it is not in conflict with the present subject matter.

From the output termination of the fiber bundle 1021, the laser beam is imaged by means of illumination transfer lenses 1301, 1302 onto the objective lens in use 1201, which is operative to focus the illumination onto a wafer 1100 being inspected. Appropriate alternative objective lenses 1201' can be swung into place on an objective revolver 1200, as is known in the microscope arts. The illumination returned from the wafer is collected by the same objective lens 1201, and is deflected from the illumination path by means of a beam splitter 1202, towards a second beam splitter 1500, from where it is reflected through the imaging lens 1203, which images the light from the wafer onto the detectors of the imager, with one of the detectors represented in FIG. 11 at 1206. In this example, only a single detector and optical path is shown for purposes of example. In practice, the path of light can vary, such as if light is split into multiple portions for detection. In this example, the second beam splitter 1500 is used to separate the light going to the imaging functionality from the light used in the auto-focus functionality, which is directed by means of the auto-focus imaging lens 1501 to the auto-focus detector 1502.

When dark field illumination is required for the imaging in hand, a dark field side illumination source 1231 is used to project the required illumination beam 1221 onto the wafer 1100. This example shows a diffuser (or diffusers) 1242 included in the illumination path between source 1231 and wafer 1100, along with an objective lens 1244. Diffuser(s) 1242 can be configured in accordance with aspects of the examples discussed above.

When orthogonal dark field, or obscured reflectance dark field illumination is required for the imaging in hand, an alternative dark field illumination source 1230 is used to project the required illumination beam 1232 via the obscured reflectance mirror 1240 onto the wafer 1100 orthogonally from above.

FIG. 11 indicates sources 1300, 1231, and 1230 at different locations. However, any or all of sources 1300, 1230, and 1231 may comprise the same light source, with the bright field, dark field, and obscured reflectance dark field effects achieved through moving the source(s) and/or redirecting illumination to the appropriate angle using one or more optical components. Further, it is to be understood that other arrangements for laser illumination and/or other illumination methods entirely could be used in conjunction with the present subject matter.

Although this and other examples discussed the use of light-shaping diffusers in the context of dark field illumination, it will be understood that one or more diffusers could be used along with the source(s) used for bright-field, obscured reflectance dark-field, and/or other types of illumination. As just mentioned, the different types of illumination may be achieved by moving a source and/or optically redirecting the illuminating light via mirrors and the like. The component(s) used to redirect light could be included after the diffuser so that the diffuser could be used for the different types of illumination or the diffuser could be included in the optical path for only certain types of illumination.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. In the example of FIG. 10, an image processing system 99 includes parallel configured image processing channels 90 for image grabbing by an image grabber 92, an image buffer 94, a defect detection unit 96, a defect file 98, and control/data links 101. Image data acquired by focal plane assembly 30 featuring twenty-four two-dimensional CCD matrix photo-detectors is processed in parallel, whereby each of the twenty-four CCD matrix photo-detectors communicates separately, in parallel to the other CCD matrix photo-detectors of focal plane assembly 30, with image grabber 92, via twenty-four separate image processing channels 90. Instead of processing image data using a single serial channel of 48 megapixels at a CCD frame speed acquisition rate of 60 times per second (resulting in a single channel with a very high, 3 gigapixels per second processing rate), each of the twenty-four or more separate image processing channels 90 having about 2 megapixels of image data, acquired at a rate of 60 times per second, is used for processing at a moderate rate of tens of megapixels per second. Image processing system 99 is in communication with central control system 20 via control/data links 101.

As another example, the tool may be connected to suitable hardware for image analysis, or image data may be provided to such hardware in any other manner.

Any suitable type(s) of analysis may be used to determine the presence or absence of defects. For example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

The above discussion is for purposes of example only with regard to illumination and imaging techniques. The present subject matter can be utilized in the context of any suitable inspection tool.

The detectors can comprise any suitable number, type, or combination of light-sensing elements. The underlying sensing can be based on any suitable technology. For instance, in various embodiments, one or more of the following types of detector types can be used: CCD, CMOS, PMT, and/or avalanche photodiode detectors.

The detectors may be of any suitable type. For example, one or more detectors may comprise an area detector, such as a matrix of photo-sensors producing 2 dimensional image data. As another example, one or more detectors can comprise a TDI line detector, i.e. a matrix of photo-sensors which produces 1 dimensional image data over time. As another example, one or more detectors can comprise a line detector i.e. a line of photo-sensors which produces 1 dimensional line image. In certain embodiments, a detector can comprise a "point detector," where each detector signal represents a pixel.

It will be appreciated that, in some embodiments in which light sensing and imaging is based on point detection, such as when PMT and/or avalanche photodiode detectors are used, the illumination and/or imaging hardware will need to be varied appropriately from the example arrangements discussed above in conjunction with FIGS. 10 and 11. For example, embodiments of a tool using PMT and/or avalanche photodiode detectors can include some sort of scanning mechanism to variably illuminate spots on the wafer or other object(s) under inspection. For instance, a suitable illumination source (such as an argon laser or another laser) can be used in conjunction with an acousto-optical deflector to scan one or more illuminating beams across the wafer or other object(s) under inspection.

As one example of inspecting using a scanning source, a sawtooth pattern in the time domain can be used while the stage moves the wafer orthogonally to the movement of the illuminating beam. The imaging optics can be arranged to appropriately collect light from the illuminating beam as reflected or otherwise scattered by the wafer. Exemplary details of an inspection system including a scanning illumination source can be found in U.S. Pat. No. 5,699,447, which is incorporated by reference herein in its entirety to the extent it does not conflict with the present subject matter. Exemplary discussion of line detection can be found in U.S. Pat. No. 6,724,473, which is incorporated by reference herein in its entirety to the extent it does not conflict with the present subject matter.

When TDI or line detection is used, illumination and relative movement of the wafer should be adjusted accordingly, with the image acquisition hardware/software also suitably configured. For instance, as is known in the art, when TDI detection is used, continuous illumination is applied while the imaging location on the wafer or other object is varied.

Similarly, the hardware/software used for image acquisition/analysis should be appropriately configured for embodiments in which point detection is used. Namely, rather than capturing an entire field of view instantaneously, the imaging hardware images a series of points or lines (which may each comprise one or more pixels) from which the entire image of the wafer can be constructed.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. An optical inspection tool comprising:
a light source configured to direct light to an object under inspection so that light impinging on the object illuminates a first portion of the object;
an imaging system operative to image a second portion of the object; and
at least one light shaping diffuser in an optical path between the light source and the object under inspection, wherein (i) the light shaping diffuser is configured so that a shape of the illuminated first portion of the object is essentially identical to a shape of the imaged second portion of the object, and (ii) the light shaping diffuser is further configured to convert an input angular distribution of the light from the light source so that the illuminating light has a rectangular distribution.

2. The inspection tool set forth in claim 1, wherein the inspection tool is configured so that the object under inspection is illuminated in dark-field mode.

3. An optical inspection tool comprising:
a light source configured to direct light to an object under inspection so that light impinging on the object illuminates a first portion of the object;
an imaging system operative to image a second portion of the object; and
at least one light shaping diffuser in an optical path between the light source and the object under inspection, wherein (i) the light shaping diffuser is configured so that a shape of the illuminated first portion of the object is essentially identical to a shape of the imaged second portion of the object, and (ii) the light shaping diffuser is further configured to convert an input angular distribution of the light from the light source so that the illuminating light has a quadrangular distribution.

4. An optical inspection tool comprising:
a light source configured to direct light to an object under inspection so that light impinging on the object illuminates a first portion of the object;
an imaging system operative to image a second portion of the object; and
at least one light shaping diffuser in an optical path between the light source and the object under inspection, wherein the light shaping diffuser is configured to adjust a distribution of light from the light source so that an intensity of light impinging on the object in the illuminated first portion, but outside the imaged second portion, is minimized.

5. An optical inspection tool comprising:
a light source configured to direct light to an object under inspection so that light impinging on the object illuminates a first portion of the object;
an imaging system operative to image a second portion of the object; and
at least one light shaping variable diffuser in an optical path between the light source and the object under inspection, wherein the inspection tool is configured so that the object under inspection is illuminated in dark-field mode, and the light shaping variable diffuser is configured to adjust a distribution of the light from the light source so as to minimize an intensity of the light impinging on the object in the illuminated first portion, but outside the imaged second portion.

6. An optical inspection tool comprising:
a light source configured to direct light to an object under inspection so that light impinging on the object illuminates a first portion of the object;
an imaging system operative to image a second portion of the object; and
at least one light shaping variable diffuser in an optical path between the light source and the object under inspection, wherein the inspection tool is configured so that the object under inspection is illuminated in dark-field mode, and the light shaping variable diffuser is configured to adjust a distribution of the light from the light source so as to increase a uniformity of the light impinging on the object across the illuminated first portion.

7. An optical inspection tool comprising:
a light source configured to direct light to an object under inspection and illuminate a first portion of the object in dark-field mode;
an imaging system operative to image a second portion of the object; and
a light shaping diffuser in an optical path between the light source and the object under inspection, the diffuser configured so that when light from any given point on the light source impinges on the object, the light illuminates essentially a same portion of the object as light from any other given point.

8. An electro-optical inspection method comprising:
directing light from a light source to an object under inspection and illuminating a first portion of the object;
prior to the light impinging the object, diffusing the light from the light source;
imaging a second portion of the object; and
analyzing at least one image so as to identify one or more defects or suspected defects on the object, wherein diffusing the light from the light source comprises: (i) tuning the light so that a shape of the illuminated first portion is essentially identical to a shape of the imaged second portion, and (ii) converting an input angular distribution of the light from the light source so that the illuminating light has a rectangular distribution.

9. The inspection method set forth in claim 8, wherein the object under inspection is illuminated in dark-field mode.

10. An electro-optical inspection method comprising:
directing light from a light source to an object under inspection and illuminating a first portion of the object;
prior to the light impinging the object, diffusing the light from the light source;
imaging a second portion of the object; and
analyzing at least one image so as to identify one or more defects or suspected defects on the object, wherein diffusing the light from the light source comprises: (i) tuning the light so that a shape of the illuminated first portion is essentially identical to a shape of the imaged second portion, and (ii) converting an input angular distribution of the light from the light source so that the illuminating light has a quadrangular angular distribution.

11. An electro-optical inspection method comprising:
directing light from a light source to an object under inspection and illuminating a first portion of the object;
prior to the light impinging the object, diffusing the light from the light source;
imaging a second portion of the object; and
analyzing at least one image so as to identify one or more defects or suspected defects on the object, wherein diffusing the light from the light source comprises adjusting a distribution of light falling in the illuminated first portion so that an intensity of light in the illuminated first portion, but outside the imaged second portion, is minimized.

12. An electro-optical inspection method comprising:
directing light from a light source to an object under inspection and illuminating a first portion of the object;
prior to the light impinging the object, diffusing with a variable diffuser the light from the light source;
imaging a second portion of the object; and
analyzing at least one image so as to identify one or more defects or suspected defects on the object, wherein illuminating the first portion of the object includes illuminating the first portion of the object in dark-field, and wherein diffusing the light from the light source includes adjusting a distribution of the light from the light source so as to minimize an intensity of light impinging on the object in the illuminated first portion, but outside the imaged second portion.

13. An electro-optical inspection method comprising:
directing light from a light source to an object under inspection and illuminating a first portion of the object;
prior to the light impinging the object, diffusing with a variable diffuser the light from the light source;
imaging a second portion of the object; and
analyzing at least one image so as to identify one or more defects or suspected defects on the object, wherein illuminating the first portion of the object includes illuminating the first portion of the object in dark-field mode, and wherein diffusing the light from the light source includes adjusting a distribution of the light from the light source so that the uniformity of light impinging on the object in the illuminated first portion is increased.

14. An optical inspection method comprising:
directing light from a light source to an object under inspection to illuminate a first portion of the object in dark-field mode;
prior to impinging the object, diffusing the light from the light source so that, when impinging the object, light directed to the object from any given part of the light source illuminates a portion having essentially a same size as any other portion illuminated by a different part of the light source;
imaging a second portion of the object; and
analyzing at least one image so as to identify one or more defects or suspected defects on the object.

* * * * *